United States Patent [19]

Radunz et al.

[11] 4,080,458
[45] Mar. 21, 1978

[54] THIAPROSTAGLANDINS

[75] Inventors: Hans-Eckart Radunz; Josef Krämer; Manfred Baumgarth; Dieter Orth, all of Darmstadt, Germany

[73] Assignee: Merck Patent Gesellschaft mit beschrankter Haftung, Darmstadt, Germany

[21] Appl. No.: 576,140

[22] Filed: May 9, 1975

[30] Foreign Application Priority Data

May 11, 1974 Germany .............................. 2422924

[51] Int. Cl.² .................... C07C 177/00; A61K 31/19; A61K 31/215
[52] U.S. Cl. ............................. 424/263; 260/294.8 G; 260/332.2 A; 260/514 D; 260/520 C; 260/516; 424/275; 424/308; 424/317; 424/305; 560/10; 560/9; 560/121
[58] Field of Search .............. 260/468 D, 514 D, 470; 424/305, 317, 263, 275

[56] References Cited

U.S. PATENT DOCUMENTS 3,932,487 1/1976 Kramer et al. ........................ 260/468

Primary Examiner—Robert Gerstl
Attorney, Agent, or Firm—Millen & White

[57] ABSTRACT

13-Thiaprostanoic acid derivatives of the formula

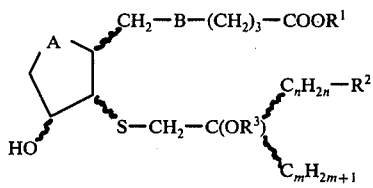

wherein A is —CO— or —CHOH—, B is —CH$_2$—CH$_2$— or —CH=CH—, R$^1$ is H or alkyl of 1 to 4 carbon atoms, m is a whole number from 0 to 5, n is a whole number from 0 to 3 or, when B is —CH=CH—, additionally 4, 5, 6, 7, 8 or 9, R$^2$ is alkoxy of 1 to 4 carbon atoms, phenoxy, pyridyl, thienyl, naphthyl, phenyl substituted by F, Cl, Br, OH, OCH$_3$ or OF$_3$ or phenoxy substituted by F, Cl, Br, OH, OCH$_3$, CH$_3$ or CF$_3$ or, when B is —CH=CH—, additionally hydrogen, phenyl or tolyl, R$^3$ is H, methyl or ethyl, possess pharmacological activity, including blood pressure lowering activity.

13 Claims, No Drawings

THIAPROSTAGLANDINS

BACKGROUND OF THE INVENTION

The invention relates to novel 13-thiaprostanoic acid derivatives.

Structurally related compounds are the subject of prior-filed U.S. application Ser. No. 416,183, filed Nov. 15, 1973, U.S. Pat. No. 3,932,487, and German Application P 22 56 537.3, filed Nov. 17, 1972.

SUMMARY OF THE INVENTION

In a composition aspect, this invention relates to novel 13-thiaprostanoic acid derivatives of the general Formula I

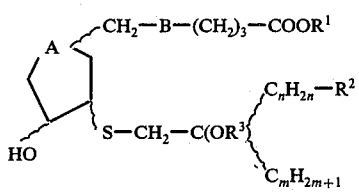

wherein A is —CO— or —CHOH—, B is —CH$_2$—CH$_2$— or —CH=CH—, R$^1$ is H or alkyl of 1 to 4 carbon atoms, $m$ is a whole number from 0 to 5, $n$ is a whole number from 0 to 3 or, when B is —CH=CH—, additionally 4, 5, 6, 7, 8 or 9, R$^2$ is alkoxy of 1 to 4 carbon atoms, phenoxy, pyridyl, thienyl, naphthyl, phenyl substituted by F, Cl, Br, OH, OCH$_3$ or OF$_3$ or phenoxy substituted by F, Cl, Br, OH, OCH$_3$, CH$_3$ or CF$_3$ or, when B is —CH=CH—, additionally hydrogen, phenyl or tolyl, R$^3$ is H, methyl or ethyl, and the wavy line (∼∼∼) means the thus-indicated bonds can be in the α- or β- position, and the physiologically acceptable salts thereof.

In another composition aspect, this invention relates to pharmaceutical compositions comprising a compound of Formula I.

In process aspects, this invention relates to processes for the production of compounds of Formula I and for their use as pharmacologics.

DETAILED DISCUSSION

The compounds of Formula I contain at least 3 asymmetric C-atoms on the five-membered ring. When A is —CHOH—, there are four centers of asymmetry in the ring. Further centers of asymmetry can also occur in the thioether side chain. Therefore, the compounds of Formula I can occur in a number of stereoisomeric forms. However, as a rule they are obtained as racemic mixtures.

Besides the individual racemates and racemic mixtures, the compounds of this invention include the optically-active isomers of Formula I.

In a process aspect, this invention relates to a process for the preparation of compounds of Formula I, and their physiologically acceptable salts, which comprises (a) reacting a compound of Formula II

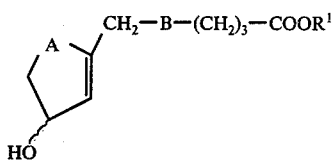

wherein A, B and R$^1$ have the values given above, with a compound of Formula III

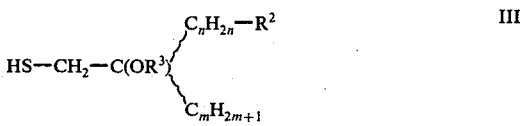

wherein R$^2$, R$^3$, $m$ and $n$ have the values given above, or (b) reacting a compound of Formula IV

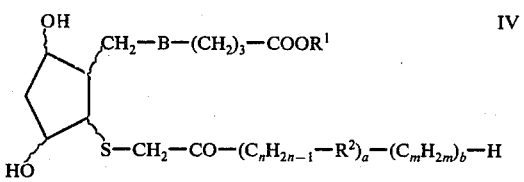

A is 1 or 0, $b$ is 0 or 1 and B, R$^1$, R$^2$, $m$ and $n$ have the values given above, with a compound of Formula V $$M—(C_2H_{2n-1}—R^2)_c—(C_mH_{2m})_d—H \qquad V$$

wherein M is lithium, MgCl, MgBr or MgI, preferably MgCl or MgBr, $c$ is 0 or 1, $d$ is 1 or 0, whereby $a + b = 1$, $c + d = 1$ and $a + c = 1$, and R$^2$, $m$ and $n$ have the values given above, or (c) reacting a compound otherwise corresponding to Formula I but wherein at least one hydroxyl group and/or the carbonyl group and/or the COOR$^1$ group is present in functionally modified form, with a solvolyzing agent.

Additionally, a compound of Formula I wherein A = —CO— can be converted into another compound of Formula I wherein A = —CHOH— by reaction with a reducing agent, and/or a compound of Formula I wherein R$^1$ = H, can be converted into another compound of Formula I wherein R$^1$ = alkyl of 1 to 4 carbon atoms, by reaction with an esterifying agent and/or a compound of Formula I can be converted into another compound of Formula I by reaction with a solvolyzing agent, and/or a compound of Formula I can be separated into its racemates and/or enantiomers, and/or a free acid of Formula I wherein R$^1$ = H, can be converted into a physiologically acceptable salt thereof by treatment with a base, or can be liberated from a salt thereof by treatment with an acid.

Specifically contemplated classes of compounds defined by Formula I are those wherein (a) A is —CHOH and the OH group is in the α-position;

(b) A is —CHOH and the OH group is in the β-position;

(c) B is —CH$_2$CH$_2$, including those of both (a) and (b);

(d) B is —CH=CH—, preferably those in the cis configuration, including those of both (a) and (b);

(e) R$^1$ is preferably hydrogen but alternatively is alkyl, preferably straight chain of up to 4 carbon atoms, e.g., methyl, ethyl, propyl or n-butyl, but alternatively branched chain, e.g., isopropyl or tert.-butyl, including each of (a) – (d), above;

(f) $m$ is any whole number from 0 to 5 and preferably is 0, 1, 2, or, when $n$ is 5 and $R^2$ is H, 5, so that $C_mH_{2m+1}$ is, besides hydrogen when m = 0, a bridging alkyl grup of 1 to 5 carbon atoms, preferably straight-chain, e.g., methyl, ethyl, propyl, butyl or pentyl, or alternatively branched chain, e.g., isopropyl or isobutyl, including each of (a)-(e), above;

(g) $n$ is any whole number from 0 to 9, but when B is —CH═CH— and $R^2$ is H, is preferably 5, 6 or 7 and when $R^2$ is other than H, is preferably 0 or 1, including each of (a)-(f), above;

(h) $R^2$ is alkoxy, including each of (a)-(g), above;

(i) $R^2$ is phenoxy or substituted phenoxy, including each of (a)-(g), above;

(j) $R^2$ is phenyl or substituted phenyl, including each of (a)-(g), above;

(k) $R^2$ is naphthyl, including each of (a)-(g), above;

(l) $R^2$ is pyridyl, including each of (a)-(g), above;

(m) $R^2$ is thienyl, including each of (a)-(g), above;

(n) B is —CH═CH—, preferably those in the cis configuration and $R^2$ is H, phenyl or tolyl.

In those compounds of Formula I in which $C_nH_{2n}$ is branched alkylene, $C_mH_{2m+1}$ is, because of possible steric hindrance, ordinarily straight chain alkyl when m is 1 or more, preferably methyl or ethyl, particularly when the branching is at the 1-position of the $C_nH_{2n}$ group. If $C_nH_{2n}$ is branched alkylene, generally any branching in the $C_mH_{2m+1}$ group is as far removed as possible from the 1-position of that group.

$C_nH_{2n}$, besides being a C—H single bond when $n = 0$ and $R^2 = $ H or a C—C or C—O single bond when $n = 0$ and $R^2$ is other than H, can also be alkylene of 1 to 3 carbon atoms, preferably methylene, ethylidene or isopropylidene. When B is —CH═CH—, $C_nH_{2n}$ can additionally be alkylene of 4 to 9 carbon atoms, preferably straight chain alkylene of 4 to 9 carbon atoms, e.g., tetramethylene, pentamethylene, hexamethylene or heptamethylene but also branched alkylene of 4 to 9 carbon atoms, e.g., —CH(CH₃)CH₂CH₂—, —CH₂CH(CH₃)CH₂—, —C(CH₃)₂CH₂—, —CH(CH₃)CH(CH₃)—, —CH(C₂H₅)CH₂—, —CH(CH₃)CH₂CH₂CH₂—, —CH₂CH(CH₃)CH₂CH₂—, —C(CH₃)₂CH₂CH₂—, —CH(CH₃)CH(CH₃)CH₂—, —CH(C₂H₅)CH₂CH₂—, —CH(CH₃)CH₂CH₂CH₂CH₂—, —C(CH₃)₂CH₂CH₂CH₂—, —CH(CH₃)CH(CH₃)CH₂CH₂—, —CH(CH₃)CH₂CH₂CH₂CH₂CH₂—, —CH(CH₃)CH(CH₃)CH₂CH₂CH₂—, —CH₂CH₂CH₂CH₂C(CH₃)₂—, —CH(CH₃)—(CH₂)₆— and —C(CH₃)₂—(CH₂)₆—.

When $R^2 = $ H in the group $C_nH_{2n}$—$R^2$, in addition to being hydrogen when $n = 0$, that group preferably is alkyl of 1 to 9 carbon atoms, preferably straight chain alkyl, e.g., methyl, ethyl, propyl, butyl, pentyl, hexyl, heptyl, octyl or nonyl, but more preferably is alkyl of 3 to 9 carbon atoms branched in the 1-position thereof such as isopropyl, sec.-butyl, tert.-butyl, 1-methylbutyl, 1-methylpentyl, 1,1-dimethylbutyl, 1-ethylbutyl, 1,2,2-trimethylpropyl, 1,1,2-trimethylpropyl, 1-ethyl-2-methylpropyl, 1-ethyl-1-methylpropyl, 1-methylhexyl, 1,1-dimethylpentyl, 1-ethylpentyl, 1,1-dimethylhexyl, 1,1-dimethylheptyl, 1,3,3-trimethylbutyl or 1,1,2,2-tetramethylpropyl; and can also be, e.g., 3,3-dimethylbutyl or 4,4-dimethylpentyl.

$R^2$ is methoxy, ethoxy, phenoxy, 2-pyridyl, 3-pyridyl, 4-pyridyl, 2-thienyl, 3-thienyl, 1-naphthyl, 2-naphthyl, phenyl mono, di- or trisubstituted by F, Cl, Br, OH, OCH₃ or CF₃ or phenoxy mono-, di- or trisubstituted by F, Cl, Br, OH, OCH₃, CH₃ or CF₃ or, when B is —CH═CH—, then $R^2$ can also be hydrogen, phenyl or tolyl. When $R^2$ is substituted phenyl or a substituted phenoxy, it is preferably monosubstituted, in the o-position or preferably in the m- or p-position.

$R^2$ is, e.g., preferably m-fluorophenyl, p-fluorophenyl, m-chlorophenyl, p-chlorophenyl, p-bromophenyl, p-hydroxyphenyl, p-methoxyphenyl, m-trifluoromethylphenyl, p-trifluoromethylphenyl, phenoxy, m-fluorophenoxy, p-fluorophenoxy, m-chlorophenoxy, p-chlorophenoxy, p-bromophenoxy, p-hydroxyphenoxy, p-methoxyphenoxy, p-methylphenoxy, m-trifluoromethylphenoxy or p-trifluoromethylphenoxy, but also can be, for example, 2,4-dichloro, 3,4-dichloro-, 2,4-dibromo-, 2,4-dimethyl-, 3,4-dimethyl-, 2,4-dimethoxy-, 2,3-dimethoxy-, 2,4,6-trimethyl- or 3,4,5-trimethoxy-phenyl or -phenoxy.

$R^3$ is preferably hydrogen.

Especially preferred are those compounds of Formula I in which at least one of the $R^1$, $R^2$, $R^3$, A, $m$ and $n$ has one of the above preferred values.

Some of these preferred groups of compounds are those of Formulae Ia to Io, which otherwise correspond to Formula I but wherein:

(Ia) $R^1 = $ H;
(Ib) $R^1 = $ methyl or ethyl;
(Ic) A = —CO—;
(Id) A = —CHOH-;
(Ie) B = —CH═CH—;
(If) $n = 0$ or 1;
(Ig) $m = 1$;
(Ih) $R^2 = $ m-fluorophenyl, p-fluorophenyl, m-chlorophenyl, p-chlorophenyl, m-fluorophenoxy, p-fluorophenoxy, m-chlorophenoxy or p-chlorophenoxy;
(Ii) $R^1$, $R^3 = $ A = —CO—, B = —CH₂—CH₂— and $R^2 = $ m-fluorophenyl, p-fluorophenyl, m-chlorophenyl, p-chlorophenyl, m-fluorophenoxy, p-chlorophenoxy; p-fluorophenoxy, m-chlorophenoxy or p-chlorophenoxy;
(Ij) $R^1 = $ methyl or ethyl, $R^3 = $ H, A = —CO—, B = —CH₂—CH₂— and $R^2 = $ m-fluorophenyl, p-fluorophenyl, m-chlorophenyl, p-chlorophenyl, m-fluorophenoxy, p-fluorophenoxy, m-chlorophenoxy or p-chlorophenoxy;
(Ik) $R^1$, $R^3 = $ H, A = —CHOH—, B = —CH₂CH₂— and $R^2 = $ m-fluorophenyl, p-fluorophenyl, m-chlorophenyl, p-chlorophenyl, m-fluorophenoxy, p-fluorophenoxy, m-chlorophenoxy or p-chlorophenoxy;
(Il) $R^1 = $ methyl or ethyl, $R^3 = $ H, A = —CHOH—, B = —CH₂—CH₂— and $R^2 = $ m-fluorophenyl, p-fluorophenyl, m-chlorophenyl, p-chlorophenyl, m-fluorophenoxy, p-fluorophenoxy, m-chlorophenoxy or p-chlorophenoxy;
(Im) $R^1 = $ H, methyl or ethyl, $R^3 = $ H, A = —CO— or —CHOH—, B = —CH═CH—, $C_nH_{2n}$—$R^2 = $ pentyl, hexyl, heptyl, 1-methylpentyl or 1,1-dimethylpentyl and $C_mH_{2m+1} = $ H or methyl.

The compounds of Formula I are structurally related to the prostaglandins derived from 7-(2-octyl-cyclopentyl)-heptanoic acid (prostanoic acid) and are derived from 13-thiaprostanoic acid.

The reactions described hereinafter for the preparation of compounds of Formula I and starting compounds for the preparation thereof, are known and analogous reactions. Reaction conditions to be employed can be taken from the standard works of preparative organic chemistry, e.g., HOUBEN-WEYL, Methoden der organischen Chemie, Georg Thieme Verlag, Stuttgart, or ORGANIC SYNTHESES, J. Wiley, New York, London, Sydney.

The compounds of Formulae II to V are known or can be prepared from known compounds in analogy with known processes. For example, 7-(3-hydroxy-5-oxo-1-cyclopentenyl)-5-heptenoic acid methyl ester is described in TETRAHEDRON LETTERS, 1973, Volume 25, p. 2313-2316. 7-(3-Hydroxy-5-oxo-1-cyclopentenyl)heptanoic acid is described, for example, in REC. TRAV. CHIM. 87, p. 1421-1434 (1968). 7-(3,5-Dihydroxy-1-cyclopentenyl)heptanoic acid can be prepared therefrom by reduction of the carbonyl group with a suitable reduction agent, preferably a complex metal hydride. The thiols of Formula III are obtainable from the corresponding $2-(C_nH_{2n}-R^1)-2-C_mH_{2m+1}$-oxiranes by reaction with $H_2S$. Compounds of Formula IV are obtainable, for example, from the cyclopentene derivatives of Formula II by addition of an ethylene ketal to a compound of the formula $HS-CH_2-CO-(C_nH_{2n-1}-R^2)_a-(C_mH_{2m})_b-H$ and hydrolysis.

The compounds which otherwise correspond to Formula I but in which at least one hydroxyl group and/or a carbonyl group and/or a $COOR^1$ group is present in functionally modified form preferably are prepared according to the same processes by which compounds of Formula I are obtainable, starting with compounds in which the corresponding hydroxyl group and/or a carbonyl group and/or a $COOR^1$ group is present in functionally modified form. Such functionally modified groups are those which are easily split off but, as a rule, are stable towards compounds of Formula V.

Functionally modified OH groups are preferably OH groups esterified with a saturated or unsaturated aliphatic, cycloaliphatic or aromatic substituted or unsubstituted carboxylic acid or sulfonic acid, or with an inorganic acid. Preferred carboxylic acid esters are those of fatty acids of 1 to 18, preferably 1 to 6 carbon atoms, e.g., formic, acetic, butyric and isobutyric acid, as well as pivalic, trichloroacetic, benzoic, p-nitrobenzoic, palmitic, stearic or oleic acid. Preferred sulfonic acid esters are esters of alkyl-sulfonic acids of 1 to 6 carbon atoms, e.g., methane- or ethane-sulfonic acid, or of aryl-sulfonic acids of 6 to 10 carbon atoms, e.g., benzene-, p-toluene-, 1- and 2-naphthalene-sulfonic acid, as well as esters of substituted sulfonic acids, such as, for example, 2-hydroxyethane- and 4-bromobenzene-sulfonic acids. Preferred inorganic acid esters are sulfates and phosphates.

Functionally modified OH groups can also be etherified OH groups which can be readily cleaved, e.g., aralkoxy of preferably 7 to 19 carbon atoms, e.g., benzyloxy, p-methyl-benzyloxy, 1- and 2-phenylethoxy, diphenylmethoxy, triphenylmethoxy and 1- or 2-naphthylmethoxy; alkyl of preferably up to 6 carbon atoms, especially methoxy, ethoxy and tert.-butoxy; tetrahydropyranyloxy; and trialkylsilyloxy, preferably trimethylsilyloxy.

Functionally modified keto groups preferably are hemiketals, e.g., $-C(OH)(OR^4)-$, ketals, e.g., $-C(OR^4)_2$ and cyclic ketals, e.g., ethylene and propylene ketals, in which the $R^4$ groups can be the same or different and, as a rule, are lower alkyl of 1 to 6 carbon atoms. Since the $R^4$ groups are present as protective groups and are not present in the end products of this invention, their exact structure is not critical.

Preferred functionally modified $COOR^1$ groups are those which, under mild reaction conditions, especially in a basic, neutral or only weakly acidic medium, can be converted into a $COOR^1$ group. Such functionally modified $COOR^1$ groups are preferably $-CON_3$, $-CN$, $-C(=NH)OR^5$, $-C(=NR^5)OR^6$, $-COSR^5$, $-CSOR^5$, $-CSSR^5$, $-C(OR^5)_3$ or $-COOR^7$ wherein $R^5$ and $R^6$ are the same or different and, besides H, can be any low molecular organic radical, the structure of which is not critical since it is not present in the end products of this invention, for example alkyl of up to 6 carbon atoms, $R^7$ can, in fact, have the same values as $R^5$ and $R^6$, except those given for $R^1$. For example, $R^7$ can be an organo-silicon radical, preferably trialkylsilyl, e.g., trimethylsilyl or dimethyl-tert.-butyl-silyl.

The reaction of a compound of Formula II with a thiol of Formula II takes place, as a rule, in the presence of a basic catalyst and in the presence or absence of an inert solvent, at temperatures of about $-20°$ to $+50°$, preferably $0°$ to $30°$. As solvents, preferred are alcohols, such as methanol or ethanol, also hydrocarbons, such as benzene or toluene; as well as water and liquid ammonia. Suitable basic catalysts are, e.g., alkali metal and alkaline earth metal hydroxides, e.g., NaOH, KOH or $Ca(OH)_2$; alkali metal alcoholates, such as $NaOCH_3$, $NaOC_2H_5$ or K-tert.-$C_4H_9$; basic salts, preferably carbonates or acetates, such as $K_2CO_3$ or $NaOCOCH_3$; ammonia; amines, such as triethylamine, tert.-butylamine, cyclohexylamine, dicyclohexylamine, dimethylaniline, piperidine, pyrrolidine, pyridine, quinoline, diaza-bicyclo[2,2,2]octane or diaza-bicyclo[3,4,0]nonene; and quaternary ammonium hydroxides, such as tetramethyl ammonium hydroxide or benzyl trimethyl ammonium hydroxide.

The reaction of a ketone of Formula IV with an organo-metallic compound of Formula V is conducted in solvents conventional for such reactions, preferably ethers, such as diethyl ether, 1,2-dimethoxyethane, tetrahydrofuran (THF), hydrocarbons, such as benzene, toluene, xylene or a mixture of these solvents, preferably at temperatures of about $-25°$ to $+20°$.

The reaction of compounds otherwise corresponding to Formula I but in which at least one hydroxyl group and/or the carbonyl group and/or the $COOR^1$ group is present in a functionally modified form with solvolyzing agents is carried out, e.g., at temperatures of $-20°$ to $40°$, usually in the presence of an acidic or preferably a basic catalyst, using an inert solvent.

Solvolyzing agents are preferably hydrolyzing agents, such as pure water or water in admixture with organic solvents, e.g., alcohols, such as methanol, ethanol, propanol, isopropanol, butanol, tert.-butyl alcohol, amyl alcohol, 2-methoxyethanol or 2-ethoxyethanol; ethers, such as diethyl ether, THF, dioxan or ethylene glycol dimethyl ether, acids, such as formic acid, acetic acid, propionic acid or butyric acid; esters, such as ethyl acetate or butyl acetate; ketones, such as acetone; amides, such as dimethyl formamide (DMF) or hexamethyl phosphoric acid triamide (HMPT); nitriles, such as acetonitrile; sulphoxides, such as dimethyl sulphoxide (DMSO); sulfones, such as tetrahydrothiophene-S,S-dioxide; as well as mixtures of these solvents.

The reaction with solvolyzing agents is usually conducted in the presence of an acidic or basic catalyst. Suitable acidic catalysts include inorganic acids, e.g., hydrochloride, sulfuric, phosphoric or hydrobromic acid and organic acids, e.g., chloroacetic acid, trichloroacetic acid or trifluoroacetic acid; methane-, ethane-, benzene- or p-toluene-sulfonic acid. Suitable basic catalysts include alkali metal and alkaline earth metal hydroxide, e.g., sodium, potassium or calcium hydroxide, and basic salts, e.g., sodium or potassium carbonate. Organic bases can also be used as basic catalysts, for example, ethyl-, diethyl-, triethyl-, isopropyl-, n-butyl- or tri-n-butylamine, ethanolamine, triethanolamine, cyclohexylamine, dimethylaniline, pyrrolidine, piperidine, morpholine, pyridine, α-picoline or quinoline; or quaternary ammonium hydroxides, e.g., tetramethyl ammonium hydroxide or benzyl trimethyl ammonium hydroxide. An excess of the catalyst can also be employed instead of a solvent.

The solvolysis reaction times are ordinarily about one hour to about 48 hours at temperatures of about −5° to about 80°, preferably room temperature.

A compound of Formula I wherein A = —CO— can be reduced to the corresponding alcohol, e.g., with metal hydrides, especially complex metal hydrides. The reduction potential of the hydrides should not be so great that the COOR$^1$ group is also reduced. Examples of suitable reducing agents are sodium borohydride, possibly in the presence of lithium bromide; as well as lithium borohydride and especially complex trialkyl lithium borohydrides, e.g., lithium hexyllimonyl-borane, or boron hydrides, e.g., lithium perhydro-9b-boraphenalyl hydride; calcium borohydride, magnesium borohydride, lithium and sodium alkoxy aluminum hydrides, e.g., LiAl(O-tert.—C$_4$H$_9$)$_3$H, sodium trialkoxy borohydrides, e.g., sodium trimethoxy borohydride.

The reduction is advantageously carried out in an inert solvent, for example, an alcohol, e.g., methanol, ethanol or isopropyl alcohol, an ether, e.g., diethyl ether, tetrahydrofuran or dioxan, or in water or in a mixture of these solvents at temperatures of −20° to 40°, preferably room temperature. Reaction times usually are between 15 minutes and 6 hours.

An ester of Formula I (R$^1$ = alkyl with 1 to 4 carbon atoms) can be prepared from an acid of Formula I (R$^1$ = H) by reaction with an esterifying agent. Esterifying agents are, for example, alcohols of up to 4 carbon atoms, preferably in the presence of an inorganic or organic acid, e.g., HCl, HBr, HI, H$_2$SO$_4$, H$_2$PO$_3$, trifluoroacetic acid, a sulfonic acid, e.g., benzene-sulfonic acid or p-toluene-sulfonic acid, or in the presence of an acidic ion exchanger; diazoalkanes of up to 4 carbon atoms, preferably diazomethane; olefins (e.g., isobutylene), preferably in the presence of acidic catalysts (e.g., ZnCl$_2$, BF$_3$, H$_2$SO$_4$, aryl-sulfonic acid, pyrophosphoric acid, boric acid, oxalic acid); alkyl halides of up to 4 carbon atoms, preferably bromides, e.g., ethyl, propyl, isopropyl or butyl bromide, as well as the corresponding chlorides or iodides; carboxylic acid or sulfonic acid alkyl esters, in which the acid moiety can be as desired and the alkyl moiety contains up to 4 carbon atoms, preferably methyl, ethyl, propyl, isopropyl or butyl acetate, formate, methyl-sulfonate, -ethyl-sulfonate or p-toluene-sulfonate; and especially also dialkyl sulfuric acid esters of up to 4 carbon atoms, e.g., dimethyl sulfate or diethyl sulfate.

The esterification expediently takes place in an inert, preferably water-free solvent, for example an ether, e.g., diethyl ether or THF, an alcohol, preferably one of the above-mentioned alcohols of up to 4 carbon atoms or in a hydrocarbon, e.g., petroleum ether, hexane, benzene or toluene, or in a mixture of these solvents, at temperatures of −10° to 40°, preferably room temperature. Reaction times are usually between 30 minutes and 20 hours.

Esters of Formula I (R$^1$ = alkyl of 1 to 4 carbon atoms) can be converted by solvolysis into other compounds of Formula I (preferably wherein R$^1$ = H). Basic hydrolysis to the acids of Formula I (or their salts) is preferred. Aqueous media, for example, mixtures of water and alcohols, preferably lower alcohols, e.g., methanol or ethanol, or water soluble glycols or ether, e.g., ethylene glycol or methyl ether, ethylene glycol dimethyl ether, THF or dioxane, are preferred as are reaction temperatures of 0° to 40°, preferably room temperature. Reaction times usually are about one hour to 12 hours.

Free carboxylic acids of Formula I (R$^1$ = H) can be converted by reaction with a base, into their physiologically acceptable metallic and ammonium salts, e.g., alkali metal, including sodium, potassium and magnesium, calcium and other metallic salts and ammonium salts, e.g., dimethyl- and diethyl-ammonium, mono-ethanol-, diethanol- and triethanol-ammonium, cyclohexyl-ammonium, dicyclohexyl-ammonium and dibenzylethylene-diammonium salts. Free acids of Formula I can be liberated from their metallic and ammonium salts by treatment with a strong acid, especially a mineral acid, e.g., hydrochloric or sulfuric acid.

Compounds of Formula I are ordinarily obtained as mixtures of various stereoisomeric forms, usually as mixtures of racemates. Individual racemates can be isolated from mixtures of racemates and obtained in pure form, for example, by recrystallization of the mixture of racemates themselves or of readily recrystallizing derivatives, by distillation and especially by chromatographic methods, including both adsorption chromatographic and partition chromatographic techniques.

The racemates can be separated into their optical antipodes according to known methods described in the literature. Chemical separation is preferred. Thus, one can react an optically-active base with the carboxyl group of a compound of Formula I, for example, to form the diastereomeric salts with optically-active amines, e.g., quinine, cinchonidine, brucine, cinchonine, hydroxydrindamine, morphine, 1-phenylethylamine, 1-naphthylethylamine, phenoxynaphthylmethylamine, quinidine, strychnine, basic amino acids, such as lysine and arginine and amino acid esters. In a similar manner, ester diastereomers can be prepared by esterification of carboxylic acids of Formula I (R$^1$ = H) with optically-active alcohols, such as borneol, methol, octan-2-ol. The diastereomeric salts or esters obtained can be separated by crystallization and the optically-active compounds liberated from the mixture in a conventional manner.

The other functional groups present in compounds of Formula I can also be employed for the formation of diastereomers. For example, one can esterify OH groups with optically-active acids, such as (+)- and (−)-tartaric acid or campheric acid, or react keto groups with optically-active hydrazines, such as menthyl-hydrazine, and obtain the pure enantiomers from these derivatives.

It is also possible to obtain optically-active compounds of Formula I employing optically-active starting compounds.

The 13-thiaprostanoic acid derivatives of Formula I and their pharmaceutically acceptable salts possess valuable pharmacological properties including blood pressure-lowering activity. Such activity can be demonstrated on a barbiturate-narcotized cat by continuous infusion. In this test, the arterial blood pressure is recorded kymographically. The test compound is infused in aqueous propylene glycol solution over a period of 10 minutes. They can be administered like the known compound prostaglandin-$E_1$.

The novel 13-thiaprostanoic acid derivatives of this invention also exhibit vasodilatory, antiphlogistic, diuretic, bronchial-relaxing, gastric juice secretion-, thrombocyte aggregation-, lipid decomposing- and noradrenaline liberation-inhibiting, as well as nasal mucous membrane decongesting activities, which also can be determined by conventional test methods. They also have a luteolytic effect, especially when A is —CH($OR^3$)—, and exercise an influence on the ovary transport through the Fallopian tube, nidation and female fertility.

The compounds of Formula I and their physiologically acceptable salts are thus useful as pharmaceuticals and as intermediates for the production of other pharmaceuticals.

The novel compounds of this invention can be used in human and veterinary medicine as pharmaceuticals, preferably in admixture with solid, liquid and/or semi-liquid pharmaceutically acceptable carriers, including those organic or inorganic materials which are suitable for parenteral, enteral or topical administration and which do react with the active compounds, such as, for example, water, vegetable oils, benzyl alcohols, polyethylene glycols, gelatine, lactose, starch, magnesium stearate, talc, vaseline, cholesterol. For parenteral administration, especially useful are solutions, preferably oily or aqueous solutions, as well as suspensions, emulsions or implants. For enteral administration, suitable forms include tablets, dragees, syrups, juices and suppositories. For topical administration, salves, creams and powders are useful. The pharmaceutical compositions can be sterilized and/or mixed with adjuvant materials, such as lubricating, preserving, stabilizing or wetting agents, emulsifiers, salts for the influencing of the osmotic pressure, buffer substances, coloring, flavoring and/or aroma materials.

The compounds of this invention are preferably administered in a dosage of 0.01 to 200 mg. per dosage unit, the exact dosage as usual being dependent upon the treated species, the form of administration and the purpose of the treatment and therefore can be below or above this range.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the compounds hereinafter, their IR spectra (IR) are characterized by listing their main absorption bands (as a film). The NMR spectra (NMR) thereof were measured in $CDCl_3$ against tetramethylsilane and the signals are given in ppm ($m$ = multiplet, $q$ = quartet, $t$ = triplet, $d$ = duplet and $s$ = singlet).

PREPARATION

Wash 20 g. of a 20% sodium hydride dispersion in paraffin oil three times with 30 ml. dry n-pentane, remove the solvent, add thereto 33 g. trimethyl sulfoxonium iodide, then drop therein 100 ml. dimethyl sulfoxide, stir for 20 minutes at room temperature until the gas evolution is ended, add dropwise thereto a solution of 14.2 g. heptan-2-one in 15 ml. dimethyl sulfoxide, stir for a further 2 hours, add thereto, with ice cooling, 500 ml. water, extract three times with 250 ml. amounts of ether, wash the combined ether extracts with water, dry with sodium sulfate and distill off the solvent to obtain, after fractionation distillation of the residue, 2-methyl-2-pentyl-oxirane as a colorless liquid; bp = 55° (20 mm. Hg.).

Pass hydrogen sulfide, with ice cooling, into 150 ml. methanol until the weight increase amounts to 3.2 g., add thereto a solution of 370 mg. diethylamine in 11 ml. methanol and subsequently 4.8 g. 2-methyl-2-pentyl-oxirane in 18 ml. methanol, again pass hydrogen sulfide into the solution for 15 minutes, leave standing for 12 hours at room temperature, distill off the solvent, dissolve the residue in 50 ml. petroleum ether (b.p. = 50°-70°), wash with water, dry over sodium sulfate and distill off the solvent to obtain as the residue, 2-hydroxy-2-methyl-heptanethiol as a colorless liquid;
IR: 920, 1140, 1380, 1465, 2570 and 3450 $cm^{-1}$;
NMR: signals at 0.96 ppm, 1.26 ppm, 2.27 ppm and 2.67 ppm.

EXAMPLE 1

Melt 0.3 g. 7-(3-hydroxy-5-oxo-1-cyclopentenyl)-heptanoic acid, add thereto 0.6 g. 2-hydroxy-3-p-fluorophenoxy-2-methylpropylthiol, cool to 0°, add thereto 0.4 ml. piperidine, leave standing for 45 minutes at room temperature, then mix the reaction mixture with 15 ml. $CHCl_3$ and 4 ml. 1N aqueous HCl, separate off the organic phase, extract the aqueous phase with $CHCl_3$, wash the combined organic phases with water, dry over $MgSO_4$, distill off the solvent and obtain, after chromatographic purification (silica gel/chloroform: methanol = 9:1), 11,15dihydroxy-15-methyl-16-p-fluorophenoxy-9-oxo-13-thia- 17,18,19,20-tetranorprostanoic acid as oil.
IR: 1215, 1500, 1710, 1740 and 3350 $cm^{-1}$;
NMR: 1.4 (s), 2.3 (t), 3.9 (s), 4.3 (m), 6.8 – 7.1 (m).

Analogously, from 7-(3-hydroxy-5-oxo-1-cyclopentenyl)heptanoic acid, by reaction with a corresponding thiol of Formula III, there is obtained:
11,15-dihydroxy-15-methyl-16-phenoxy-9-oxo-13-thia-17,18,19,20-tetranorprostanoic acid,
11,15-dihydroxy-15-methyl-16-p-chlorophenoxy-9-oxo-13-thia-17,18,19,20-tetranorprostanoic acid,
11,15-dihydroxy-15-methyl-16-p-bromophenoxy-9-oxo-13-thia-17,18,19,20-tetranorprostanoic acid,
11,15-dihydroxy-15-methyl-16-p-hydroxyphenoxy-9-oxo-13-thia-17,18,19,20-tetranorprostanoic acid,
11,15-dihydroxy-15-methyl-16-p-methoxyphenoxy-9-oxo-13-thia-17,18,19,20-tetranorprostanoic acid,
11,15-dihydroxy-15-methyl-16-p-tolyloxy-9-oxo-13-thia-17,18,19,20-tetranorprostanoic acid,
11,15-dihydroxy-15-methyl-16-m-chlorophenoxy-9-oxo-13-thia-17,18,19,20-tetranorprostanoic acid,
11,15-dihydroxy-15-methyl-16-m-trifluoromethylphenoxy-9-oxo-13-thia-17,18,19,20-tetranorprostanoic acid,
11,15-dihydroxy-15-methyl-16-p-trifluoromethylphenoxy-9-oxo-13-thia-17,18,19,20-tetranorprostanoic acid,
11,15-dihydroxy-15-methyl-16-(2,4-dichlorophenoxy)-9-oxo-13-thia-17,18,19,20-tetranorprostanoic acid,
11,15-dihydroxy-15-methyl-16-(2,4-dimethoxyphenoxy)-9-oxo-13-thia-17,18,19,20-tetranorprostanoic acid, 11,15-dihydroxy-15-methyl-16-(2,4,6-trimethylphenoxy)-9-oxo-13-thia-17,18,19,20-tetranorprostanoic acid,
11,15-dihydroxy-15-methyl-16-(3,4,5-trimethoxyphenoxy)-9-oxo-13-thia-17,18,19,20-tetranorprostanoid acid,
11,15-dihydroxy-15-methyl-16-methoxy-9-oxo-13-thia-17,18,19,20-tetranorprostanoic acid,
11,15-dihydroxy-15-methyl-16-ethoxy-9-oxo-13-thia-17,18,19,20-tetranorprostanoic acid,
11,15-dihydroxy-16-phenoxy-9-oxo-13-thia-17,18,19,20-tetranorprostanoic acid,
11,15-dihydroxy-16-p-fluorophenoxy-9-oxo-13-thia-17,18,19,20-tetranorprostanoic acid,
11,15-dihydroxy-16-m-trifluoromethylphenoxy-9-oxo-13-thia-17,18,19,20-tetranorprostanoic acid,
IR: 1160, 1230, 1490, 1590, 1700, 1730, 2950 and 3410 cm$^{-1}$,
NMR: 2,3 (t), 4,1 (m), 4,2 – 4,5 (m), 7,0 – 7,5 (m),
11,15-dihydroxy-16-p-chlorophenoxy-9-oxo-13-thia-17,18,19,20-tetranorprostanoic acid,
11,15-dihydroxy-16-p-trifluorometylphenoxy-9-oxo-13-thia-17,18,19,20-tetranorprostanoic acid, and
11,15-dihydroxy-16-p-methoxyphenoxy-9-oxo-13-thia-17,18,19,20-tetranorprostanoic acid.

EXAMPLE 2

To a mixture of 0.3 g. 7-(3-hydroxy-5-oxo-1-cyclopentenyl)heptanoic acid, 6 ml. dry ethanol and 0.6 g. 2-p-fluorophenyl-2-hydroxy-propylthiol, add at 0° 0.4 ml. piperidine, leave the mixture standing for 2 hours at room temperature, add 20 ml. H$_2$O, 4 ml. 1N HCl and 30 ml. CHCl$_3$ to the reaction mixture and work up as described in Example 1 to obtain 11,15-dihydroxy-15-p-fluorophenyl-9-oxo-13-thia-17,18,19,20-tetranorprostanoic acid as an oil.
IR: 1220, 1505, 1605, 1708, 1740 and 3400 cm$^{-1}$;
NMR: 1.61 (s), 2.3 (t), 4.2 (m), 6.9 – 7.15 (m), 7.3 – 7.5 (m).
Analogously, from 7-(3-hydroxy-5oxo-1-cyclopentenyl)-heptanoic acid, by reaction with a corresponding thiol of Formula III, there are obtained:
11,15-dihydroxy-15-p-fluorophenyl-9-oxo-13-thia-18,19,20-trinorprostanoic acid,
11,15-dihydroxy-15-p-fluorophenyl-9-oxo-13-thia-19,20-dinorprostanoic acid,
11,15-dihydroxy-15-p-fluorophenyl-9-oxo-13-thia-20-norprostanoic acid,
11,15-dihydroxy-15-p-fluorophenyl-9-oxo-13-thia-prostanoic acid,
11,15-dihydroxy-15-(3,4,5-trimethoxyphenyl)-9-oxo-13-thia-17,18,19,20-tetranor-prostanoic acid,
IR: 1130, 1600, 1670, 1710, 1740, 2950, 3450 cm$^{-1}$,
NMR: 1.63 (s), 2,3(t), 3.8(s), 4.23(g), 5.4(m), 6.63(s),
11,15-dihydroxy-15-methyl-16-m-chlorophenyl-9-oxo-13-thia-17,18,19,20-tetanorprostanoic acid,
IR: 1400, 1495, 1700, 1740, 2950, 3450 cm$^{-1}$,
NMR: 1.25(2), 2.35(t), 4.3(m), 5.6(m), 7.0 – 7.4(m),
11,15-dihydroxy-15-p-chlorophenyl-9-oxo-13-thia-prostanoic acid,
11,15-dihydroxy-15-p-bromophenyl-9-oxo-13-thia-prostanoic acid,
11,15-dihydroxy-15-p-hydroxyphenyl-9-oxo-13-thia-prostanoic acid,
11,15-dihydroxy-15-p-methoxyphenyl-9-oxo-13-thia-prostanoic acid,
11,15-dihydroxy-15-p-trifluoromethylphenyl-9-oxo-13-thia-prostanoic acid,
11,15-dihydroxy-15-p-fluorophenyl-9-oxo-13-thia-16,17,18,19,20-pentanorprostanoic acid,
11,15-dihydroxy-15-p-chlorophenyl-9-oxo-13-thia-16,17,18,19,20-pentanorprostanoic acid,
11,15-dihydroxy-15-p-methoxyphenyl-9-oxo-13-thia-16,17,18,19,20-pentanorprostanoic acid,
11,15-dihydroxy-15-p-trifluoromethylphenyl-9-oxo-13-thia-16,17,18,19,20-pentanorprostanoic acid,
11,15-dihydroxy-16-p-fluorophenyl-9-oxo-13-thia-17,18,19,20-tetranorprostanoic acid,
11,15-dihydroxy-16-p-chlorophenyl-9-oxo-13-thia-17,18,19,20,tetranorprostanoic acid,
11,15-dihydroxy-16-p-methoxyphenyl-9-oxo-13-thia-17,18,19,20-tetranorprostanoic acid,
11,15-dihydroxy-16-p-trifluoromethylpehnyl-9-oxo-13-thia-17,18,19,20-tetranorprostanoic acid,
11,15-dihydroxy-15-(2-naphthyl)-9-oxo-13-thia-17,18,19,20-tetranorprostanoic acid,
IR: 1600, 1705 – 1740 and 2900 – 3400 cm$^{-1}$;
NMR: 1.76(s), 2.28(t), 4.2(m), 7.42(m), 7.8(m);
11,15-dihydroxy-15-m-chlorophenyl-9-oxo-13-thia-17,18,19,20-tetranorprostanoic acid, and
11,15-dihydroxy-15-p-chlorophenyl-9-oxo-13-thia-17,18,19,20-tetranorprostanoic acid,
IR: 1710, 1740 and 3400 cm$^{-1}$,
NMR: 1.65(s), 2.3(t), 4.25(q), 7.3(m).

EXAMPLE 3

To a mixture of 0.3 g. 7-(3-hydroxy-5-oxo-1-cyclopentenyl)-heptanoic acid and 0.6 g. 2-hydroxy-3-p-fluorophenoxy-2-methylpropylthiol, add at 0° 0.4 ml. morpholine, leave standing for 65 minutes at room temperature and work up the reaction mixture as described in Example 1 to obtain 11,15-dihydroxy-16-p-fluorophenoxy-15-methyl-9-oxo-13-thia-17,18,19,20-tetranorprostanoic acid as an oil.
Analogously, from 7-(3-hydroxy-5-oxo-1-cyclopentenyl)-heptanoic acid, by reaction with a corresponding thiol of the Formula III, there is obtained:
11,15-dihydroxy-15-p-fluorophenoxymethyl-9-oxo-13-thia-prostanoic acid,
11,15-dihydroxy-15-p-chlorophenoxymethyl-9-oxo-13-thia-prostanoic acid,
11,15-dihydroxy-15-p-bromophenoxymethyl-9-oxo-13-thia-prostanoic acid,
11,15-dihydroxy-15-p-hydroxyphenoxymethyl-9-oxo-13-thia-prostanoic acid,
11,15-dihydroxy-15-p-methoxyphenoxymethyl-9-oxo-13-thia-prostanoic acid,
11,15-dihydroxy-15-p-trifluoromethylphenoxymethyl-9-oxo-13-thia-prostanoic acid,
11,15-dihydroxy-15-p-fluorobenzyl-9-oxo-13-thia-prostanoic acid,
11,15-dihydroxy-15-p-chlorobenzyl-9-oxo-13-thia-prostanoic acid, and
11,15-dihydroxy-15-p-methoxybenzyl-9-oxo-13-thia-prostanoic acid.

EXAMPLE 4

Melt 0.3 g. 7-(3-hydroxy-5-oxo-1-cyclopentenyl)-5-heptanoic acid, add thereto 0.6 g. 2-hydroxy-3-p-fluorophenoxy-2-methyl-propylthiol, cool to 5°, add thereto 0.4 ml. piperidine, leave standing for 45 minutes at room temperature and work up the reaction mixture as described in Example 1 to obtain 11,15-dihydroxy-15-methyl-16-p-fluorophenoxy-9-oxo-13-thia-17,18,19,20-tetranor-5-prostenoic acid.

Analogously, from 7-(3-hydroxy-5-oxo-1-cyclopentenyl)-5-heptanoic acid, by reaction with a corresponding thiol of Formula III, there is obtained:
11,15-dihydroxy-15-methyl-16-phenoxy-9-oxo-13-thia-17,18,19,20-tetranor-5-prostenoic acid,
11,15-dihydroxy-15-methyl-16-p-chlorophenoxy-9-oxo-13-thia-17,18,19,20-tetranor-5-prostenoic acid,
11,15-dihydroxy-15-methyl-16-p-bromophenyl-9-oxo-13-thia-17,18,19,20-tetranor-5-prostenoic acid,
11,15-dihydroxy-15-methyl-16-p-hydroxyphenoxy-9-oxo-13-thia-17,18,19,20-tetranor-5-prostenoic acid,
11,15-dihydroxy-15-methyl-16-p-methoxyphenoxy-9-oxo-13-thia-17,18,19,20-tetranor-5-prostenoic acid,
11,15-dihydroxy-15-methyl-16-p-tolyloxy-9-oxo-13-thia-17,18,19,20-tetranor-5-prostenoic acid,
11,15-dihydroxy-15-methyl-16-p-trifluoromethylphenoxy-9-oxo-13-thia-17,18,19,20-tetranor-5-prostenoic acid,
11,15-dihydroxy-15-methyl-16-(2,4-dichlorophenoxy)-9-oxo-13-thia-17,18,19,20-tetranor-5-prostenoic acid,
11,15-dihydroxy-15-methyl-16-(2,4-dimethoxyphenoxy)-9-oxo-13-thia-17,18,19,20-tetranor-5-prostenoic acid,
11,15-dihydroxy-15-methyl-16-(2,4,6-trimethylphenoxy)-9-oxo-13-thia-17,18,19,20-tetranor-5-prostenoic acid,
11,15-dihydroxy-15-methyl-16-(3,4,5-trimethoxyphenoxy)-9-oxo-13-thia-17,18,19,20-tetranor-5-prostenoic acid,
11,15-dihydroxy-15-methyl-16-methoxy-9-oxo-13-thia-17,18,19,20-tetranor-5-prostenoic acid, and
11,15-dihydroxy-15-methyl-16-ethoxy-9-oxo-13-thia-17,18,19,20-tetranor-5-prostenoic acid.

EXAMPLE 5

To a mixture of 0.3 g. 7-(3-hydroxy-5-oxo-1-cyclopentenyl)-5-heptenoic acid, 6 ml. dry ethanol and 0.6 g. 2-p-fluorophenyl-2-hydroxy-propylthiol, add at 0° 0.4 ml. piperidine, leave the mixture standing for 2 hours at room temperature, add to the reaction mixture 20 ml. H₂O, 4 ml. 1N HCl and 30 ml. CHCl₃ and work up as described in Example 1 to obtain 11,15-dihydroxy-15-p-fluorophenyl-9-oxo-13-thia-17,18,19,20-tetranor-5-prostenoic acid.

Analogously, from 7-(3-hydroxy-5-oxo-1-cyclopentenyl)-5-heptenoic acid, by reaction with a corresponding thiol of Formula III, there is obtained:
11,15-dihydroxy-15-p-fluorophenyl-9-oxo-13-thia-18,19,20-trinor-5-prostenoic acid.
11,15-dihydroxy-15-p-fluorophenyl-9-oco-13-thia-19,20-dinor-5-prostenoic acid,
11,15-dihydroxy-15-p-fluorophenyl-9-oxo-13-thia-20-nor-5-prostenoic acid,
11,15-dihydroxy-15-p-fluorophenyl-9-oxo-13-thia-5-prostenoic acid,
11,15-dihydroxy-15-p-chlorophenyl-9-oxo-13-thia-5-prostenoic acid,
11,15-dihydroxy-15-p-bromophenyl-9-oxo-13-thia-5-prostenoic acid,
11,15-dihydroxy-15-p-hydroxyphenyl-9-oxo-13-thia-5-prostenoic acid,
11,15-dihydroxy-15-p-methoxyphenyl-9-oxo-13-thia-5-prostenoic acid,
11,15-dihydroxy-15-p-trifluoromethylphenyl-9-oxo-13-thia-5-prostenoic acid,
11,15-dihydroxy-16-p-fluorophenyl-9-oxo-13-thia-5-prostenoic acid,
11,15-dihydroxy-16-p-chlorophenyl-9-oxo-thia-5-prostenoic acid,
11,15-dihydroxy-16-p-bromophenyl-9-oxo-13-thia-5-prostenoic acid,
11,15-dihydroxy-6-p-hydroxyphenyl-9-oxo-13-thia-5-prostenoic acid,
11,15-dihydroxy-16-p-methoxyphenyl-9-oxo-13-thia-5-prostenoic acid, and
11,15-dihydroxy-16-p-trifluoromethylphenyl-9-oxo-13-thia-5-prostenoic acid.

EXAMPLE 6

To a mixture of 0.3 g. 7-(3-hydroxy-5-oxo-1-cyclopentenyl)-5-heptenoic acid and 0.6 g. 2-hydroxy-3-p-fluorophenoxy-2-methylpropylthiol add at 0° 0.4 ml. morpholine, leave to stand for 65 minutes at room temperature and work up the reaction mixture as described in Example 1 to obtain 11,15-dihydroxy-16-p-fluorophenyl-15-methyl-9-oxo-13-thia-17,18,19,20-tetranor-5-prostenoic acid.

Analogously, from 7-(3-hydroxy-5-oxo-1-cyclopentenyl)-5-heptenoic acid, by reaction with a corresponding thiol of Formula III, there are obtained: 11,15-dihydroxy-15-p-fluorophenoxymethyl-9-oxo-13-thia-5-prostenoic acid,
11,15-dihydroxy-15-p-chlorophenoxymethyl-9-oxo-13-thia-5-prostenoic acid,
11,15-dihydroxy-15-p-bromophenoxymethyl-9-oxo-13-thia-5-prostenoic acid,
11,15-dihydroxy-15-p-hydroxyphenoxymethyl-9-oxo-13-thia-5-prostenoic acid,
11,15-dihydroxy-15-p-methoxyphenoxymethyl-9-oxo-13-thia-5-prostenoic acid,
11,15-dihydroxy-15-p-trifluoromethylphenoxymethyl-9-oxo-13-thia-5-prostenoic acid,
11,15-dihydroxy-15-p-fluorobenzyl-9-oxo-thia-5-prostenoic acid,
11,15-dihydroxy-15-p-chlorobenzyl-9-oxo-13-thia-5-prostenoic acid, and
11,15-dihydroxy-15-p-methoxybenzyl-9-oxo-13-thia-5-prostenoic acid.

EXAMPLE 7

Analogously to Example 4, by the reaction of 7-(3-hydroxy-5-oxo-cyclopentyl)-5-heptenoic acid with the corresponding thiols of Formula III, there is obtained:
11,15-dihydroxy-9-oxo-13-thia-5-prostenoic acid,
11,15-dihydroxy-15-methyl-9-oxo-13-thia-5-prostenoic acid,
11,15-dihydroxy-15,16-dimethyl-9-oxo-13-thia-5-prostenoic acid,
11,15-dihydroxy-16,16-dimethyl-9-oxo-13-thia-5-prostenoic acid,
11,15-dihydroxy-15,16,16-trimethyl-9-oxo-13-thia-5-prostenoic acid,
11,15-dihydroxy-15-ethyl-9-oxo-13-thia-5-prostenoic acid,
11,15-dihydroxy-15-propyl-9-oxo-13-thia-5-prostenoic acid,
11,15-dihydroxy-15-butyl-9-oxo-13-thia-5-prostenoic acid, and
11,15-dihydroxy-15-pentyl-9-oxo-13-thia-5-prostenoic acid.

EXAMPLE 8

Analogously to Example 5, by the reaction of 7-(3-hydroxy-5-oxo-cyclopentenyl)-5-heptenoic acid with the corresponding thiols of Formula III, there is obtained:

11,15-dihydroxy-9-oxo-13-thia-20-homo-5-prostenoic acid, 11,15-dihydroxy-15-methyl-9-oxo-13-thia-20-homo-5-prostenoic acid, 11,15-dihydroxy-15,16-dimethyl-9-oxo-13-thia-20-homo-5-prostenoic acid, 11,15-dihydroxy-16,16-dimethyl-9-oxo-13-thia-20-homo-5-prostenoic acid, 11,15-dihydroxy-15,16,16-trimethyl-9-oxo-13-thia-20-homo-5-prostenoic acid, 11,15-dihydroxy-9-oxo-13-thia-20-ethyl-5-prostenoic acid, 11,15-dihydroxy-15-methyl-9-oxo-13-thia-20-ethyl-5-prostenoic acid, 11,15-dihydroxy-15,16-dimethyl-9-oxo-13-thia-20-ethyl-5-prostenoic acid, 11,15-dihydroxy-16,16-dimethyl-9-oxo-13-thia-20-ethyl-5-prostenoic acid, and 11,15-dihydroxy-15,16,16-trimethyl-9-oxo-13-thia-20-ethyl-5-prostenoic acid.

EXAMPLE 9

Analogously to Example 6, by the reaction of 7-(3-hydroxy-5-oxo-cyclopentenyl)-5-heptenoic acid with the corresponding ponding thiols of Formula III, there is obtained:

11,15-dihydroxy-15-phenyl-9-oxo-16,17,18,19,20-pentanor-13-thia-5-prostenoic acid, 11,15-dihydroxy-15-p-tolyl-9-oxo-16,17,18,19,20-pentanor-13-thia-5-prostenoic acid, 11,15-dihydroxy-15-phenyl-9-oxo-17,18,19,20-tetranor-13-thia-5-prostenoic acid, 11,15-dihydroxy-15-p-tolyl-9-oxo-17,18,19,20-tetranor-13-thia-5-prostenoic acid, 11,15-dihydroxy-16-phenyl-9-oxo-17,18,19,20-tetranor-13-thia-5-prostenoic acid, 11,15-dihydroxy-16-p-tolyl-9-oxo-17,18,19,20-tetranor-13-thia-5-prostenoic acid, 11,15-dihydroxy-15-methyl-16-phenyl-9-oxo-17,18,19,20-tetranor-13-thia-5-prostenoic acid, 11,15-dihydroxy-15-methyl-16-p-tolyl-9-oxo-17,18,19,20-tetranor-13-thia-5-prostenoic acid, 11,15-dihydroxy-15,16-dimethyl-16-phenyl-9-oxo-17,18,19,20-tetranor-13-thia-5-prostenoic acid, 11,15-dihydroxy-15,16-dimethyl-16-p-tolyl-9-oxo-17,18,19,20-tetranor-13-thia-5-prostenoic acid, 11,15-dihydroxy-16,16-dimethyl-16-phenyl-9-oxo-17,18,19,20-tetranor-13-thia-5-prostenoic acid, and 11,15-dihydroxy-16,16-dimethyl-16-p-tolyl-9-oxo-17,18,19,20-tetranor-13-thia-5-prostenoic acid.

EXAMPLE 10

Analogously to Example 6, by the reaction of 7-(3-hydroxy-5-oxo-cyclopentenyl)-5-heptenoic acid with the corresponding thiols of Formula III, there is obtained:

11,15-dihydroxy-15-phenyl-9-oxo-13-thia-5-prostenoic acid, 11,15-dihydroxy-15-p-tolyl-9-oxo-13-thia-5-prostenoic acid, 11,15-dihydroxy-15-benzyl-9-oxo-13-thia-5-prostenoic acid, and 11,15-dihydroxy-15-p-tolylmethyl-9-oxo-13-thia-5-prostenoic acid.

EXAMPLE 11

Under nitrogen at room temperature, add dropwise 1 g. 11,15-dihydroxy-15-methyl-16-p-fluorophenoxy-9-oxo-13-thia-17,18,19,20-tetranor-prostanoic acid, dissolved in 10 ml. dry THR, to a suspension of 3.3 g. LiAl (O-tert.-$C_4H_9$)$_3$H in 25 ml. dry THF, leave standing for 1 hour at room temperature, pour into 70 ml. ice-cold 1N HCl, extract with $CHCl_3$ and work up the organic phase as described in Example 1 to obtain 9,11,15-trihydroxy-15-methyl-16-p-fluorophenoxy-13-thia-17,18,19,20-tetranor-prostanoic acid as oil.

IR: 1220, 1710 and 3400 cm$^{-1}$;

NMR: 1.37(s), 2.30(t), 3.85(s), 4.14(m), 6.7 – 7.0(m).

Analogously, from the corresponding 9-oxo compounds of Formula I, by reaction with LiAl (O-tert.-$C_4H_9$)$_3$H, there is obtained:

9,11,15-trihydroxy-15-m-chlorophenyl-13-thia-17,18,19,20-tetranor-prostanoic acid, 9,11,15-trihydroxy-15-p-chlorophenyl-13-thia-17,18,19,20-tetranor-prostanoic acid, 9,11,15-trihydroxy-15-methyl-16-p-fluorophenyl-13-thia-17,18,19,20-tetranorprostanoic acid, 9,11,15-trihydroxy-15-methyl-16-phenoxy-13-thia-17,18,19,20-tetranorprostanoic acid, 9,11,15-trihydroxy-15-methyl-16-p-tolyloxy-13-17,18,19,20-tetranorprostanoic acid, 9,11,15-trihydroxy-15-methyl-16-p-chlorophenyl-13-thia-17,18,19,20-tetranorprostanoic acid, 9,11,15-trihydroxy-15-methyl-16-methoxy-13-thia-17,18,19,20-tetranorprostanoic acid, 9,11,15-trihydroxy-15-methyl-16-ethoxy-13-thia-17,18,19,20-tetranorprostanoic acid, 9,11,15-trihydroxy-15-methyl-16-p-chlorophenyl-13-thia-17,18,19,20-tetranorprostanoic acid, 9,11,15-trihydroxy-16-p-fluorophenyl-13-thia-17,18,19,20-tetranorprostanoic acid, 9,11,15-trihydroxy-16-p-fluorophenoxy-13-thia-13-thia-17,18,19,20-tetranorprostanoic acid, 9,11,15-trihydroxy-16-phenoxy-13-thia-17,18,19,20-tetranorprostanoic acid, 9,11,15-trihydroxy-16-p-tolyloxy-13-thia-17,18,19,20-tetranorprostanoic acid, 9,11,15-trihydroxy-16-p-chlorophenoxy-13-thia-17,18,19,20-tetranorprostanoic acid, 9,11,15-trihydroxy-16-methoxy-13-thia-17,18,19,20-tetranorprostanoic acid, 9,11,15-trihydroxy-16-ethoxy-13-17,18,19,20-tetranorprostanoic acid, 9,11,15-trihydroxy-16p-chlorophenyl-13-thia-17,18,19,20-tetranorprostanoic acid, 9,11,15-trihydroxy-15-methyl-16-m-chlorophenoxy-13-thia-17,18,19,20-tetranorprostanoic acid, and 9,11,15-trihydroxy-15-methyl-16-m-trifluoromethylphenoxy-13-thia-17,18,19,20-tetranorprostanoic acid.

EXAMPLE 12

Analogously to Example 11, from the corresponding 9-oxo compounds of Formula I, by reaction with LiAl-(O-tert.-$C_4H_9$)$_3$H, there is obtained:

9,11,15-trihydroxy-15-p-fluorophenyl-13-thia-prostanoic acid, 9,11,15-trihydroxy-15-p-chlorophenyl-13-thia prostanoic acid, 9,11,15-trihydroxy-15-p-bromophenyl-13-thia-prostanoic acid, 9,11,15-trihydroxy-15-p-hydroxyphenyl-13-thia-prostanoic acid, 9,11,15-trihydroxy-15-p-methoxyphenyl-13-thia-prostanoic acid,
9,11,15-trihydroxy-15-p-trifluoromethylphenyl-13-thia-prostanoic acid,
9,11,15-trihydroxy-15-phenyloxymethyl-13-thia-prostanoic acid,
9,11,15-trihydroxy-15-p-fluorophenoxymethyl-13-thia-prostanoic acid,
9,11,15-trihydroxy-15-p-tolyloxymethyl-13-thia-prostanoic acid,
9,11,15-trihydroxy-15-methoxymethyl-13-thia-prostanoic acid,
9,11,15-trihydroxy-15-ethoxymethyl-13-thia-prostanoic acid, and
9,11,15-trihydroxy-15-p-fluorobenzyl-13-thia-prostanoic acid.

EXAMPLE 13

Analogously to Example 11, from the corresponding 9-oxo compounds of Formula I, by reaction with LiAl-(O-tert.-$C_4H_9$)$_3$H, there is obtained:
9,11,15-trihydroxy-13-thia-5-prostenoic acid,
9,11,15-trihydroxy-15-methyl-13-thia-5-prostenoic acid,
IR: 1710, 2200 and 3700 $cm^{-1}$;
NMR: 0.85(t), 1.2(s), 1.0 – 2.6(m), 2.6 – 3.05 (m+s), 4.15(m), 5.1 – 5.4(m).
9,11,15-trihydroxy-15,16-dimethyl-13-thia-5-prostenoic acid,
9,11,15-trihydroxy-16,16-dimethyl-13-thia-5-prostenoic acid,
9,11,15-trihydroxy-15,16,16-trimethyl-13-thia-5-prostenoic acid,
9,11,15-trihydroxy-13-thia-20-homo-5-prostenoic acid,
9,11,15-trihydroxy-15-methyl-13-thia-20-homo-5-prostenoic acid,
9,11,15-trihydroxy-13-thia-20-ethyl-5-prostenoic acid, and
9,11,15-trihydroxy-15-methyl-13-thia-20-ethyl-5-prostenoic acid.

EXAMPLE 14

Stir a mixture of 1 g. 11,15-dihydroxy-15-methyl-16-p-fluorophenyl-9-oxo-13-thia-17,18,19,20-tetranor-5-prostenoic acid, 0.6 g. NaBH$_4$ and 15 ml. methanol for 3 hours at room temperature and then work up the reaction mixture as described in Example 11 to obtain 9,11,15-trihydroxy-15-methyl-16-p-flurophenyl-13-thia-17,18,19,20-tetranor-5-prostenoic acid as an oil.

Analogously, by reaction of the corresponding 9-oxo compounds of Formula I with NaBH$_4$, there is obtained:
9,11,15-trihydroxy-15-phenyl-13-thia-17,18,19,20-tetranor-5-prostenoic acid,
9,11,15-trihydroxy-15-p-tolyl-13-thia-17,18,19,20-tetranor-5-prostenoic acid,
9,11,15-trihydroxy-15-phenyl-13-thia-16,17,18,19,20-pentanor-5-prostenoic acid,
9,11,15-trihydroxy-15-p-fluorophenyl-13-thia-16,17,18,19,20-pentanor-5-prostenoic acid,
9,11,15-trihydroxy-15-p-tolyl-13-thia-16,17,18,19,20pentanor-5-prostenoic acid,
9,11,15-trihydroxy-16-phenyl-13-thia-17,18,19,20-tetranor-5-prostenoic acid,
9,11,15-trihydroxy-16-p-fluorophenyl-13-thia-17,18,19,20-tetranor-5-prostenoic acid,
9,11,15-trihydroxy-16-p-tolyl-13-thia-17,18,19,20-tetranor-5-prostenoic acid,
9,11,15-trihydroxy-15-methyl-16-phenyl-13-thia-17,18,19,20-tetranor-5-prostenoic acid, and
9,11,15-trihydroxy-15-methyl-16-p-tolyl-13-thia-17,18,19,20-tetranor-5-prostenoic acid.

EXAMPLE 15

Mix 100 mg. 11,15-dihydroxy-15-methyl-16-p-fluorophenoxy-9-oxo-13-thia-17,18,19,20-tetranor-prostenoic acid, dissolved in 10 ml. diethyl ether, with excess ethereal diazomethane solution until no more nitrogen evaluation can be seen. Distill off the solvent and chromatographically purify (silica gel/benzene: chloroform = 1:1) residue to obtain 11,15-dihydroxy-15-methyl-16-p-fluorophenoxy-9-oxo-13-thia-17,18,19,20-tetranor-prostenoic acid methyl ester.

Analogously, from the free acids of Formula I, preparable according to Examples 1 to 9, by reaction with diazomethane, the corresponding methyl esters are obtained, especially
11,15-dihydroxy-15-methyl-16-phenoxy-9-oxo-13-thia-17,18,19,20-tetranor-prostanoic acid methyl ester,
11,15-dihydroxy-15-methyl-16-p-tolyloxy-9-oxo-13-thia-17,18,19,20-tetranor-prostanoic acid methyl ester,
11,15-dihydroxy-15-methyl-16-methoxy-9-oxo-13-thia-17,18,19,20-tetranor-prostanoic acid methyl ester,
11,15-dihydroxy-15-methyl-16-ethoxy-9-oxo-13-thia-17,18,19,20-tetranor-prostanoic acid methyl ester,
11,15-dihydroxy-15-p-fluorophenyl-9-oxo-13-thia-17,18,19,20-tetranor-prostanoic acid methyl ester,
11,15-dihydroxy-15-p-fluorophenyl-9-oxo-13-thia-prostanoic acid methyl ester,
11,15-dihydroxy-16-p-fluorophenyl-9-oxo-13-thia-prostanoic acid methyl ester,
11,15-dihydroxy-15-p-fluorophenoxymethyl-9-oxo-13-thia-prostanoic acid methyl ester,
11,15-dihydroxy-15-p-fluorobenzyl-9-oxo-13-thia-prostanoic acid methyl ester,
11,15-dihydroxy-15-methyl-16-phenoxy-9-oxo-13-thia-17,18,19,20-tetranor-5-prostenoic acid methyl ester,
11,15-dihydroxy-15-methyl-16-p-tolyloxy-9-oxo-13-thia-17,18,19,20-tetranor-5-prostenoic acid methyl ester,
11,15-dihydroxy-15-methyl-16-methoxy-9-oxo-13-thia-17,18,19,20-tetranor-5-prostenoic acid methyl ester,
11,15-dihydroxy-15-methyl-16-ethoxy-9-oxo-13-thia-17,18,19,20-tetranor-5-prostenoic acid methyl ester,
11,15-dihydroxy-15-p-fluorophenyl-9-oxo-13-thia-17,18,19,20-tetranor-5-prostenoic acid methyl ester,
11,15-dihydroxy-15-p-fluoropyhenyl-9-oxo-13-thia-5-prostenoic acid methyl ester,
11,15-dihydroxy-16-p-fluorophenyl-9-oxo-13-thia-5-prostenoic acid methyl ester,
11,15-dihydroxy-15-p-fluorophenoxymethyl-9-oxo-13-thia-5-prostenoic acid methyl ester,
11,15-dihydroxy-15-p-fluorobenzyl-9-oxo-13-thia-5-prostenoic acid methyl ester,
11,15-dihydroxy-9-oxo-13-thia-5-prostenoic acid methyl ester,
11,15-dihydroxy-15-methyl-9-oxo-13-thia-5-prostenoic acid methyl ester,
11,15-dihydroxy-15,16-dimethyl-9-oxo-13-thia-5-prostenoic acid methyl ester,
11,15-dihydroxy-16,16-dimethyl-9-oxo-13-thia-5-prostenoic acid methyl ester,
11,15-dihydroxy-15-pentyl-9-oxo-13-thia-5-prostenoic acid methyl ester, 11,15-dihydroxy-9-oxo-13-thia-20-homo-5-prostenoic acid methyl ester, 11,15-dihydroxy-15-methyl-9-oxo-13-thia-20-homo-5-prostenoic acid methyl ester, 11,15-dihydroxy-9-oxo-13-thia-20-ethyl-5-prostenoic acid methyl ester, 11,15,dihydroxy-15-methyl-9-oxo-13-thia-20-ethyl-5-prostenoic acid methyl ester, 11,15-dihydroxy-15-phenyl-9-oxo-16,17,18,19,20-pentanor-13-thia-5-prostenoic acid methyl ester, 13,thia-5-prostenoic acid methyl ester, 11,15,dihydroxy-15-phenyl-9-oxo-17,18,19,20-tetranor-13-thia-5-prostenoic acid methyl ester, 11,15-dihydroxy-15-p-tolyl-9-oxo-17,18,19,20-tetranor-13-thia-5-prostenoic acid methyl ester, 11,15-dihydroxy-16-phenyl-9-oxo-17,18,19,20-tetranor-13-thia-5-prostenoic acid methyl ester, 11,15-dihydroxy-16-p-tolyl-9-oxo-17,18,19,20-tetranor-13-thia-5-prostenoic acid methyl ester, and 11,15-dihydroxy-15-methyl-16-phenyl-9-oxo-17,18,19,20-tetranor-13-thia-5-prostenoic acid methyl ester.

EXAMPLE 16

Analogously to Example 15, from the free acids of Formula I, preparable according to Examples 11 to 14, by reaction with diazomethane, there are obtained the corresponding methyl esters, especially 9,11,15-trihydroxy-15-methyl-16-p-fluorophenoxy-13-thia-17,18,19,20-tetranor-prostenoic acid methyl ester, 9,11,15-trihydroxy-15-methyl-16-phenoxy-13-thia-17,18,19,20-tetranor-prostanoic acid methyl ester, 9,11,15-trihydroxy-15-methyl-16-p-tolyloxy-13-thia-17,18,19,20-tetranor-prostenoic acid methyl ester, 9,11,15-trihydroxy-16-p-fluorophenyl-13-thia-17,18,19,20-tetranor-prostenoic acid methyl ester, 9,11,15-trihydroxy-16-p-fluorophenoxy-13-thia-17,18,19,20-tetranor-prostanoic acid methyl ester, 9,11,15-trihydroxy-16-phenoxy-13-thia-17,18,19,20-tetranor-prostanoic acid methyl ester, 9,11,15-trihydroxy-16-p-tolyloxy-13-thia-17,18,19,20-tetranor-prostanoic acid methyl ester, 9,11,15-trihydroxy-15-p-fluorophenyl-13-thia-prostenoic acid methyl ester, 9,11,15-trihydroxy-15-phenyloxymethyl-13-thia-prostanoic acid methyl ester, 9,11,15-trihydroxy-15-p-fluorophenoxymethyl-13-thia-prostanoic acid methyl ester, 9,11,15-trihydroxy-15-p-tolyloxymethyl-13-thia-prostanoic acid methyl ester, 9,11,15-trihydroxy-15-p-fluorobenzyl-13-thia-prostenoic acid methyl ester, 9,11,15-trihydroxy-13-thia-5-prostenoic acid methyl ester, 9,11,15-trihydroxy-15-methyl-13-thia-5-prostenoic acid methyl ester, 9,11,15-trihydroxy-15,16-dimethyl-13-thia-5-prostenoic acid methyl ester, 9,11,15-trihydroxy-16,16-dimethyl-13-thia-5-prostenoic acid methyl ester, 9,11,15-trihydroxy-13-thia-20-homo-5-prostenoic acid methyl ester, 9,11,15-trihydroxy-13-thia-20-ethyl-5-prostenoic acid methyl ester, 9,11,15-trihydroxy-15-phenyl-13-thia-17,18,19,20-tetranor-5-prostenoic acid methyl ester, 9,11,15-trihydroxy-15-p-tolyl-13-thia-17,18,19,20-tetranor-5-prostenoic acid methyl ester, 9,11,15-trihydroxy-15-phenyl-13-thia-16,17,18,19,20-pentanor-5-prostenoic acid methyl ester, 9,11,15-trihydroxy-15-p-fluorophenyl-13-thia-16,17,18,19,20-pentanor-5-prostenoic acid methyl ester, 9,11,15-trihydroxy-15-p-tolyl-13-thia-16,17,18,19,20-pentanor-5-prostenoic acid methyl ester, 9,11,15-trihydroxy-16-phenyl-13-thia-17,18,19,20-tetranor-5-prostenoic acid methyl ester, 9,11,15-trihydroxy-16-p-fluorophenyl-13-thia-17,18,19,20-tetranor-5-prostenoic acid methyl ester, and 9,11,15-trihydroxy-15-methyl-16-phenyl-13-thia-17,18,19,20-tetranor-5-prostenoic acid methyl ester.

EXAMPLE 17

(a) Analogously to Example 1, 0.28 g. 7-(3-hydroxy-5-oxo-1-cyclopentenyl)-5-heptenoic acid methyl ester are reacted with 0.6 g. 2-hydroxy-3-p-fluorophenoxy-2-methyl-propylthiol in the presence of 0.4 ml. piperidine to obtain 11,15-dihydroxy-15methyl-16-p-fluorophenoxy-9-oxo-13-thia-17,18,19,20-tetranor-5-prostenoic acid methyl ester.

(b) 0.1 g. 11,15-dihydroxy-15-methyl-16-p-fluorophenoxy-9-oxo-13-thia-17,18,19,20-tetranor-5-prostenoic acid methyl ester is stirred for 90 hours in a mixture of 2 ml. of an aqueous saturated NaCN solution and 6 ml. methanol. Saturate with NaCl, extract with chloroform, wash the organic phase with water, dry over MgSO$_4$ and distill off the solvent to obtain, after chromatographic purification of the residue (silica gel/CHCl$_3$ : CH$_3$CH = 9:1), 11,15-dihydroxy-15-methyl-16-p-fluorophenoxy-9-oxo-13-thia-17,18,19,20-tetranor-5-prostenoic acid.

(c) Add to an ethanolic sodium ethanolate solution, prepared from 0.12 g. sodium and 10 ml. dry ethanol, dropwise 2.2 g. 11,15-dihydroxy-15-methyl-16-p-fluorophenoxy-9-oxo-13-thia-17,18,19,20-tetranor-5-prostenoic acid, dissolved in 10 ml. dry diethyl ether and distill off the solvent to obtain, as the residue, the sodium salt of 11,15-dihydroxy-15-methyl-16-p-fluorophenoxy-9-oxo-13-thia-17,18,19,20-tetranor-5-prostenoic acid.

(d) Stir a mixture of 1.54 g. of the silver salt of 11,15-dihydroxy-15-methyl-16-p-fluorophenoxy-9-oxo-13-thia-17,18,19,20-tetranor-5-prostenoic acid, 0.52 g. ethyl iodide and 10 ml. dry ethanol for 4 hours at room temperature, add 20 ml. diethyl ether thereto, filter and distill off the solvent to obtain, as the residue, 11,15-dihydroxy-15-methyl-16-p-fluorophenoxy-9-oxo-13-thia-17,18,19,20-tetranor-5-prostenoic acid ethyl ester.

EXAMPLE 18

(a) To a mixture of 2.4 g. 7-(3-hydroxy-5-oxo-1-cyclopentenyl)-5-heptenoic acid, 1.9 g. 1-thioheptan-2-one ethylene ketal (preparable from 1-bromoheptan-2-one by reaction with ethylene glycol to 1-bromoheptan-2-one ethylene ketal and reaction of this compounds with NaHS) and 20 ml. dry ethanol add at 0° 2 ml. piperidine, leave standing for 2 hours at room temperature, pour the mixture in 50 ml. ice water, extract with chloroform, wash the organic phase with H$_2$O until the wash water no longer is alkaline, dry over MgSO$_4$ and distill off the solvent to obtain, as the residue, 11-hydroxy-15,15-ethylenedioxy-9-oxo-13-thia-5-prostenoic acid.

(b) 0.1 g. 11-hydroxy-15,15-ethylenedioxy-9-oxo-13-thia-5-prostenoic acid is reduced with NaBH₄ analogously to Example 14 and the 9,11-dihydroxy-15,15-ethylenedioxy-13-thia-5-prostenoic acid obtained subsequently stirred at room temperature for 2 hours with 10 ml. IN aqueous HCl and 10 ml. dioxan. The reaction mixture is saturated with NaCl extracted with benzene, the organic phase dried and the solvent distilled off to obtain, as the residue, 9,11-dihydroxy-15-oxo-13-thia-5-prostenoic acid.

(c) Add dropwise 0.37 g. 9,11-dihydroxy-15-oxo-13-thia-5-prostenoic acid, dissolved in 10 ml. dry diethyl ether, to a methyl magnesium iodide solution, prepared from 0.024 g. magnesium shavings and 0.14 g. methyl iodide in 15 ml. dry diethyl ether, stir the reaction for one hour, pour into 50 ml. saturated aqueous NH₄Cl solution, extract with diethyl ether, dry the organic phase over Na₂SO₄ and distill off the solvent to obtain, as the residue, 9,11,15-trihydroxy-15-methyl-13-thia-5-prostenoic acid.

EXAMPLE 19

Analogously to Example 1, by the addition of the corresponding thiols to the corresponding cyclopentene derivatives, there is obtained:

11,15-dihydroxy-15-(4-pyridyl)-9-oxo-13-thia-17,18,19,20-tetranorprostanoic acid methyl ester,
IR: 1600, 1740 and 3000 - 3500 cm$^{-1}$;
NMR: 1.63(s), 2.28(t), 3.70(s), 4.29(m), 7.33(m) and 8.45(m);
11,15-dihydroxy-15-(2-thienyl)-9-oxo-13-thia-17,18,19,20-tetranorprostanoic acid,
11,15-dihydroxy-15-methyl-9-oxo-13-thia-19-oxa-prosteneoic acid,
IR: 1115, 1710, 1740 and 3400 cm$^{-1}$;
NMR: 1.27(s), 2.32(t), 3.31(s), 4.22(q);
11,15-dihydroxy-15-methyl-9-oxo-13-thia-18-oxa-prostenoic acid,
IR: 1715, 1740 and 3400 cm$^{-1}$;
NMR: 1.21(t), 1.32(s), 2.31(t), 3.50(q), 4.28(q);
11,15-dihydroxy-15,19-dimethyl-9-oxo-13-thia-18-oxo-prostenoic acid,
11,15-dihydroxy-15-methyl-20-ethyl-9-oxo-13-thia-18-oxy-prostanoic acid,
11,15-dihydroxy-15,20,20-trimethyl-9-oxo-13-thia-19-oxa-prostanoic acid, and the methyl esters thereof.

EXAMPLE 20

Analogously to Example 14 from the corresponding 9-oxocompounds of Formula I (A = —CO—, B = —CH=CH), there are obtained by reaction with NaBH₄:

9,11,15-trihydroxy-16-p-fluorophenoxy-13-thia-17,18,19,20-tetranor5-prostenoic acid,
IR: 1210, 1505, 1710, 2700, 2940, 3700 cm$^{-1}$;
NMR: 1.1 - 2.6(m), 2.7 - 3.1(m), 4.05(m), 4.2(m), 5.30(m), 5.45(m), 6.85(s), 6.95(d),
9,11,15-trihydroxy-16-m-chlorophenoxy-13-thia-17,18,19,20-tetranor-5-prostenoic acid,
IR: 1710, 2400 3650 cm$^{-1}$;
NMR: 1.1 - 2.6(m), 2.6 - 3.1(m), 4.05(m,) 4.2(m), 5.3(m), 5.4(m), 5.5 - 7.4(m),
9,11-dihydroxy-15-methoxy-16-p-fluorophenoxy-13-thia-17,18,19,20-tetranor-5-prostenoic acid,
IR: 1210, 1505, 1710, 2700, 2940, 3700 cm$^{-1}$;
NMR: 1.1 - 2.6(m), 2.95(m), 3.50(s), 3.75(m), 4.0(m), 4.10 (m), 5.40(m), 5.60(m), 6.85(d), 6.95(d).

The following Examples illustrate the preparation of compositions containing a compound of Formula I or their pharmacologically compatible salts;

EXAMPLE A: Tablets

A mixture consisting of 30 g. of the sodium salt of 11,15-dihydroxy-15-methyl-16-p-fluorophenoxy-9-oxo-13-thia-17,18,19,20-tetranor-prostanoic acid, 50 g. lactose, 16 g. maize starch, 2 g. cellulose powder and 2 g. magnesium stearate is pressed in the usual manner into tablets containing 30 mg. of the active material in each tablet.

EXAMPLE B: Dragees

Analogously the Example A, tablets are formed and then coated in a conventional manner with a coating consisting of sugar, maize starch, talc and tragacanth.

Tablets and dragees are similarly obtained containing one or more other compounds of Formula I or of their physiologically acceptable salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

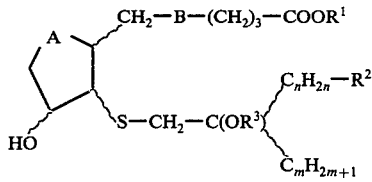

wherein A is —CO— or —CHOH—, B is —CH=CH—, R¹ is H or alkyl of 1 to 4 carbon atoms, m is a whole number from 0 to 5, n is a whole number from 1 to 9, R² is hydrogen, alkoxy of 1 to 4 carbon atoms, phenyl, tolyl, phenoxy, pyridyl, thienyl, naphthyl, phenyl substituted by F, Cl, Br, OH, OCH₃ or CF₃, or phenoxy substituted by F, Cl, Br, OH, OCH₃, CH₃ or CF₃, and R³ is H, methyl or ethyl, and the physiologically acceptable salts thereof.

2. A compound of claim 1 wherein R² is phenyl, phenoxy or phenyl or phenoxy substituted by F, Cl, Br, OH, OCH₃, CH₃ or CF₃.

3. A compound of claim 1 wherein R² is phenyl substituted by F, Cl, Br, OH, OCH₃ or CF₃.

4. A compound of claim 1 wherein R² is phenoxy substituted by F, Cl, Br, OH, OCH₃, CH₃ or CF₃.

5. A compound of claim 1 wherein R¹ is H.

6. A compound of claim 1 wherein A is —CO—.

7. A compound of claim 1 wherin A is —CHOH—.

8. A compound of claim 1 wherein R¹ is H, methyl or ethyl; R³ is H; $C_nH_{2n}$—R² is pentyl, hexyl, heptyl, 1-methylpentyl or 1,1-dimethylpentyl; and $C_mH_{2m+1}$ is H or methyl.

9. A compound of claim 1, 9,11,15-trihydroxy-15-methyl-13-thia-5-prostenoic acid.

10. A compound of claim 1, 9,11,15-trihydroxy-16-p-fluorophenoxy-17,18,19,20-tetranor-13-thia-5-prostenoic acid.

11. A compound of claim 1, 9,11,15-trihydroxy-16-m-chlorophenoxy-17,18,19,20-tetranor-13-thia-5-prostenoic acid.

12. A compound of claim 1, 9,11-dihydroxy-16-p-fluorophenoxy-15-methoxy-17,18,19,20-tetranor-13-thia-5-prostenoic acid.

13. A pharmaceutical composition comprising a blood pressure lowering amount of a compound of claim 1 in admixture with a pharmaceutically acceptable carrier.

* * * * *

UNITED STATES PATENT AND TRADEMARK OFFICE

CERTIFICATE EXTENDING PATENT TERM
UNDER 35 U.S.C. 156

Patent No.    : 4,080,458

Dated         : March 21, 1978

Inventor(s)   : Hans-Eckart Radunz et al

Patent Owner  : Merck Patent Gesellschaft
                mit beschrankter Haftung This is to certify that there has been presented to the

COMMISSIONER OF PATENTS AND TRADEMARKS an application under 35 U.S.C. 156 for an extension of the patent term. Since it appears that the requirements of the la have been met, this certificate extends the term of the patent for the period of

3 YEARS with all rights pertaining thereto as provided by 35 USC 156 (b).

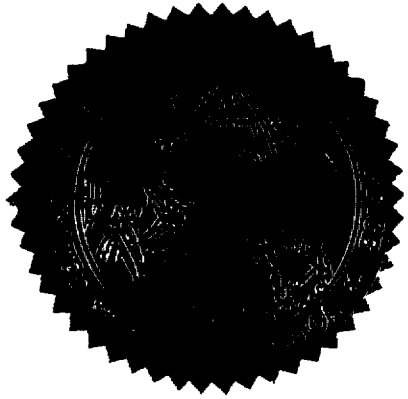

I have caused the seal of the Patent and Trademark Office to be affixed this 8th day of February, 1991.

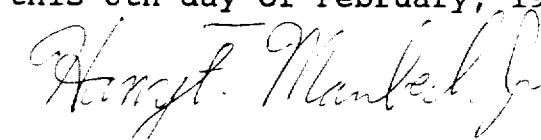

Harry F. Manbeck, Jr.
Assistant Secretary and Commissioner
   of Patents and Trademarks